United States Patent
Baker et al.

(10) Patent No.: US 9,545,326 B2
(45) Date of Patent: Jan. 17, 2017

(54) INTRALUMINAL DEVICE DELIVERY TECHNIQUE

(71) Applicant: BFKW, LLC, Grand Rapids, MI (US)

(72) Inventors: Randal S. Baker, Ada, MI (US); Frederick J. Walburn, Grand Rapids, MI (US)

(73) Assignee: BFKW, LLC, Grand Rapids, MI (US)

( * ) Notice: Subject to any disclaimer, the term of this patent is extended or adjusted under 35 U.S.C. 154(b) by 125 days.

(21) Appl. No.: 14/383,315

(22) PCT Filed: Mar. 5, 2013

(86) PCT No.: PCT/US2013/029055
§ 371 (c)(1),
(2) Date: Sep. 5, 2014

(87) PCT Pub. No.: WO2013/134227
PCT Pub. Date: Sep. 12, 2013

(65) Prior Publication Data
US 2015/0025313 A1   Jan. 22, 2015

Related U.S. Application Data

(60) Provisional application No. 61/607,338, filed on Mar. 6, 2012, provisional application No. 61/635,477, filed on Apr. 19, 2012.

(51) Int. Cl.
*A61B 1/00* (2006.01)
*A61F 5/00* (2006.01)
(Continued)

(52) U.S. Cl.
CPC ............. *A61F 5/0089* (2013.01); *A61B 1/273* (2013.01); *A61F 2/04* (2013.01); *A61F 2/95* (2013.01);
(Continued)

(58) Field of Classification Search
CPC . A61B 1/00066; A61B 1/00082; A61B 1/273; A61B 1/2733; A61B 1/27361
(Continued)

(56) References Cited

U.S. PATENT DOCUMENTS

| 4,403,604 A | 9/1983 | Wilkinson et al. |
| 4,607,618 A | 8/1986 | Angelchik |

(Continued)

FOREIGN PATENT DOCUMENTS

| RU | 2045233 C1 | 10/1995 |
| RU | 94026119 A1 | 8/1996 |

(Continued)

OTHER PUBLICATIONS

Commonly assigned copending U.S. Appl. No. 14/920,403, filed Oct. 22, 2015, entitled Bariatric Device and Method.
(Continued)

*Primary Examiner* — Timothy J Neal
(74) *Attorney, Agent, or Firm* — Gardner, Linn, Burkhart & Flory, LLP

(57) ABSTRACT

A technique for deploying an intraluminal device, such as a bariatric device, in a mammalian lumen, such as the gastrointestinal tract, includes positioning a visualization device through an orifice, such as a natural orifice, into the mammalian lumen. A deployment device having the intraluminal device mounted thereto is guided to the mammalian lumen. The intraluminal device, which has a lumen wall that is configured to the size and shape of a portion of the mammalian lumen, is at least partially deployed from the deployment device in the mammalian lumen. The at least partially deployed intraluminal device is positioned with the deployment device while a position of said intraluminal device is visualized with the visualization device.

16 Claims, 12 Drawing Sheets

(51) Int. Cl.
  *A61F 2/95*   (2013.01)
  *A61F 2/04*   (2013.01)
  *A61B 1/273*  (2006.01)
  *A61B 1/04*   (2006.01)
  *A61B 17/00*  (2006.01)
  *A61B 17/12*  (2006.01)

(52) U.S. Cl.
  CPC .... *A61F 5/0079* (2013.01); *A61B 2017/00623* (2013.01); *A61B 2017/12054* (2013.01); *A61F 2002/044* (2013.01); *A61F 2002/045* (2013.01); *A61F 2250/0039* (2013.01)

(58) Field of Classification Search
  USPC .................................. 600/104, 114, 115, 116
  See application file for complete search history.

(56)             References Cited

U.S. PATENT DOCUMENTS

| | | |
|---|---|---|
| 5,234,454 A | 8/1993 | Bangs |
| 5,306,300 A | 4/1994 | Berry |
| 5,507,755 A | 4/1996 | Gresl et al. |
| 5,662,713 A | 9/1997 | Andersen et al. |
| 5,741,279 A | 4/1998 | Gordon et al. |
| 5,820,584 A | 10/1998 | Crabb |
| 6,146,416 A | 11/2000 | Andersen et al. |
| 6,355,070 B1 | 3/2002 | Andersen et al. |
| 6,432,040 B1 | 8/2002 | Meah |
| 6,544,291 B2 | 4/2003 | Taylor |
| 6,558,400 B2 | 5/2003 | Deem et al. |
| 6,572,627 B2 | 6/2003 | Gabbay |
| 6,656,194 B1 | 12/2003 | Gannoe et al. |
| 6,675,809 B2 | 1/2004 | Stack et al. |
| 6,736,828 B1 | 5/2004 | Adams et al. |
| 6,740,121 B2 | 5/2004 | Geitz |
| 6,746,460 B2 | 6/2004 | Gannoe et al. |
| 6,755,869 B2 | 6/2004 | Geitz |
| 6,773,440 B2 | 8/2004 | Gannoe et al. |
| 6,802,868 B2 | 10/2004 | Silverman et al. |
| 6,845,776 B2 | 1/2005 | Stack et al. |
| 6,960,233 B1 | 11/2005 | Berg et al. |
| 6,981,978 B2 | 1/2006 | Gannoe |
| 6,994,095 B2 | 2/2006 | Burnett |
| 6,994,715 B2 | 2/2006 | Gannoe et al. |
| 7,025,791 B2 | 4/2006 | Levine et al. |
| 7,033,373 B2 | 4/2006 | de la Torre et al. |
| 7,033,384 B2 | 4/2006 | Gannoe et al. |
| 7,037,344 B2 | 5/2006 | Kagan et al. |
| 7,044,979 B2 | 5/2006 | Silverman et al. |
| 7,066,945 B2 | 6/2006 | Hashiba et al. |
| 7,083,629 B2 | 8/2006 | Weller et al. |
| 7,083,630 B2 | 8/2006 | DeVries et al. |
| 7,087,088 B2 | 8/2006 | Berg et al. |
| 7,097,650 B2 | 8/2006 | Weller et al. |
| 7,097,665 B2 | 8/2006 | Stack et al. |
| 7,146,984 B2 | 12/2006 | Stack et al. |
| 7,152,607 B2 | 12/2006 | Stack et al. |
| 7,220,284 B2 | 5/2007 | Kagan et al. |
| 7,232,461 B2 | 6/2007 | Ramer |
| 7,347,875 B2 | 3/2008 | Levine et al. |
| 7,431,725 B2 | 10/2008 | Stack et al. |
| 7,445,010 B2 | 11/2008 | Kugler et al. |
| 7,682,330 B2 | 3/2010 | Meade et al. |
| 7,708,752 B2 | 5/2010 | Durgin |
| 7,771,382 B2 | 8/2010 | Levine et al. |
| 7,815,589 B2 | 10/2010 | Meade et al. |
| 7,815,591 B2 | 10/2010 | Levine et al. |
| 7,846,174 B2 | 12/2010 | Baker et al. |
| 7,922,650 B2 * | 4/2011 | McWeeney ........ A61B 1/00071 600/104 |
| 7,976,488 B2 | 7/2011 | Levine et al. |
| 7,981,163 B2 | 7/2011 | Meade et al. |
| 8,029,455 B2 | 10/2011 | Stack et al. |
| 8,043,355 B2 | 10/2011 | Shin et al. |
| 8,100,931 B2 | 1/2012 | Baker et al. |
| 8,137,301 B2 | 3/2012 | Levine et al. |
| 8,162,871 B2 | 4/2012 | Levine et al. |
| 8,282,598 B2 | 10/2012 | Belhe et al. |
| 8,372,087 B2 | 2/2013 | Baker et al. |
| 8,529,431 B2 | 9/2013 | Baker et al. |
| 8,672,831 B2 | 3/2014 | Baker et al. |
| 8,801,599 B2 | 8/2014 | Baker et al. |
| 8,894,670 B2 | 11/2014 | Baker et al. |
| 9,375,338 B2 | 6/2016 | Baker et al. |
| 2001/0020189 A1 | 9/2001 | Taylor |
| 2002/0032487 A1 | 3/2002 | Dua et al. |
| 2002/0091395 A1 | 7/2002 | Gabbay et al. |
| 2003/0040804 A1 | 2/2003 | Stack et al. |
| 2003/0040808 A1 | 2/2003 | Stack et al. |
| 2004/0092892 A1 | 5/2004 | Kagan et al. |
| 2004/0117031 A1 | 6/2004 | Stack et al. |
| 2004/0138761 A1 | 7/2004 | Stack et al. |
| 2004/0143342 A1 | 7/2004 | Stack et al. |
| 2004/0148034 A1 | 7/2004 | Kagan |
| 2004/0172141 A1 | 9/2004 | Stack et al. |
| 2004/0220682 A1 | 11/2004 | Levine et al. |
| 2005/0080395 A1 | 4/2005 | Levine et al. |
| 2005/0096728 A1 | 5/2005 | Ramer |
| 2005/0125020 A1 | 6/2005 | Meade et al. |
| 2005/0197715 A1 | 9/2005 | Kugler et al. |
| 2005/0228504 A1 | 10/2005 | Demarais |
| 2005/0245788 A1 | 11/2005 | Gerber |
| 2005/0245957 A1 | 11/2005 | Starkebaum et al. |
| 2005/0247320 A1 | 11/2005 | Stack et al. |
| 2005/0251176 A1 | 11/2005 | Swanstrom et al. |
| 2005/0283235 A1 | 12/2005 | Kugler et al. |
| 2006/0020277 A1 | 1/2006 | Gostout et al. |
| 2006/0036293 A1 | 2/2006 | Whitehurst et al. |
| 2006/0064120 A1 | 3/2006 | Levine et al. |
| 2006/0074473 A1 | 4/2006 | Gertner |
| 2006/0089571 A1 | 4/2006 | Gertner |
| 2006/0149307 A1 | 7/2006 | Durgin |
| 2006/0155375 A1 | 7/2006 | Kagan et al. |
| 2006/0161139 A1 | 7/2006 | Levine et al. |
| 2006/0190019 A1 | 8/2006 | Gannoe et al. |
| 2006/0247721 A1 | 11/2006 | Maschino et al. |
| 2006/0253131 A1 | 11/2006 | Wolniewicz, III |
| 2006/0264699 A1 | 11/2006 | Gertner |
| 2006/0265082 A1 | 11/2006 | Meade et al. |
| 2007/0005147 A1 | 1/2007 | Levine et al. |
| 2007/0010866 A1 | 1/2007 | Dann et al. |
| 2007/0112409 A1 * | 5/2007 | Wu ........................ A61F 2/95 623/1.12 |
| 2007/0166396 A1 | 7/2007 | Badylak et al. |
| 2007/0179590 A1 | 8/2007 | Lu et al. |
| 2007/0208429 A1 | 9/2007 | Leahy |
| 2007/0233221 A1 | 10/2007 | Raju |
| 2007/0276432 A1 | 11/2007 | Stack et al. |
| 2007/0293716 A1 | 12/2007 | Baker et al. |
| 2008/0015523 A1 | 1/2008 | Baker |
| 2008/0015618 A1 | 1/2008 | Sonnenschein et al. |
| 2008/0065122 A1 | 3/2008 | Stack et al. |
| 2008/0065136 A1 | 3/2008 | Young |
| 2008/0215076 A1 | 9/2008 | Baker |
| 2008/0312678 A1 | 12/2008 | Pasricha |
| 2009/0138071 A1 | 5/2009 | Cheng et al. |
| 2009/0177215 A1 | 7/2009 | Stack et al. |
| 2009/0240340 A1 | 9/2009 | Levine et al. |
| 2009/0248171 A1 | 10/2009 | Levine et al. |
| 2010/0030017 A1 | 2/2010 | Baker et al. |
| 2010/0063518 A1 | 3/2010 | Baker et al. |
| 2010/0114130 A1 | 5/2010 | Meade et al. |
| 2010/0198237 A1 | 8/2010 | Baker et al. |
| 2010/0256775 A1 | 10/2010 | Belhe et al. |
| 2011/0009690 A1 | 1/2011 | Belhe et al. |
| 2011/0092879 A1 | 4/2011 | Baker et al. |
| 2012/0089168 A1 | 4/2012 | Baker et al. |
| 2012/0289991 A1 | 11/2012 | Baker |
| 2013/0123811 A1 | 5/2013 | Baker et al. |
| 2013/0296913 A1 | 11/2013 | Foote et al. |
| 2014/0018611 A1 | 1/2014 | Baker et al. |

(56) References Cited

U.S. PATENT DOCUMENTS

| | | | |
|---|---|---|---|
| 2014/0114230 A1 | 4/2014 | Baker et al. | |
| 2014/0121585 A1 | 5/2014 | Baker et al. | |
| 2016/0151233 A1 | 6/2016 | Baker et al. | |

FOREIGN PATENT DOCUMENTS

| | | | |
|---|---|---|---|
| WO | 9412136 A1 | 6/1994 | |
| WO | 0135834 A1 | 5/2001 | |
| WO | 0185034 A1 | 11/2001 | |
| WO | 02060328 A1 | 8/2002 | |
| WO | 02094105 A2 | 11/2002 | |
| WO | 2004064685 A1 | 8/2004 | |
| WO | 2005037152 A1 | 4/2005 | |
| WO | 2006044640 A1 | 4/2006 | |
| WO | 2007092390 A2 | 8/2007 | |
| WO | 2009048398 A1 | 4/2009 | |
| WO | 2011116025 A1 | 9/2011 | |

OTHER PUBLICATIONS

Commonly assigned copending U.S. Appl. No. 14/518,414, filed Oct. 20, 2014, entitled Mucosal Capture Fixation of Medical Device.
Schembre, Drew, "Advances in Esophageal Stenting: the Evolution of Fully Covered Stents for Malignant and Benign Disease," Adv. Ther., Springer Healthcare, Apr. 1, 2010, pp. 1-13.
Commonly assigned copending U.S. Appl. No. 14/572,230, filed Dec. 16, 2014, entitled Endoscopic Fixation of a Medical Device Using Mucosal Capture.
International Search Report of the International Searching Authority from corresponding Patent Cooperation Treaty (PCT) Patent Application No. PCT/US13/29055, mailed May 28, 2013.
"Obesity: Super-Sized Medical Device Market", Start-Up, Mar. 2003, Technology Strategies (Long Article), pp. 1-10 and a cover page.
Andrew S. Lowe, M.D. and Maria B. Sheridan, M.D., "Esphogeal Stenting", Seminars in Interventional Radiology, vol. 21, No. 3, 2004, pp. 157-166.
"Polyflex® Espohageal Stent", Silicone Covered Stent, Boston Scientific, pp. 1-2 and p. 1 of 2.
Andrew F.R. Dixon, Johgn B. Dixon, and Paul E. O'Brien, "Laparoscopic Adjustable Gastric Banding Induces Prolonged Satiety: A Randomized Blind Crossover Study", The Journal of Clinical Endocrinology & Metabolism , pp. 813-819, 2005.
Roman, S. et al., "Intragastric balloon for 'non-morbid' obesity: a retrospective evaluation of tolerance and efficacy," Obes. Surg., 2004, 14(4), 539-44, abstract, [on-line], [found Apr. 17, 2009, from Pubmed database].
Busetto, L. et al., "Preoperative weight loss by intragastric balloon in super-obese patients treated with laparoscopic gastric banding: a case-control study," Obes Surg., 2004, 14(5), 671-6, abstract, [on-line], [found Apr. 17, 2009, from Pubmed database].
Summary of Official Action dated Oct. 29, 2009, from the Israel Patent Office in a patent application corresponding to the present application.
Lowe, Andrew S., M.D. and Sheridan, Maria B., M.D., "Esophageal Stenting," annotated by Israel Patent Office (2004).
Abstract and claims of U.S. Pat. No. 6,960,233 annotated by the Israel Patent Office (Nov. 1, 2005).
Commonly assigned copending U.S. Appl. No. 14/314,444, filed Jun. 25, 2014, entitled Bariatric Device and Method.
International Preliminary Report on Patentability from corresponding Patent Cooperation Treaty Patent Application No. PCT/US2013/029055 mailed Sep. 18, 2014.
Commonly assigned co-pending U.S. Appl. No. 15/163,030, filed May 24, 2016, entitled Intraluminal Device and Method of Fixation.
Commonly assigned co-pending U.S. Appl. No. 15/211,034, filed Jul. 15, 2016 entitled Bariatric Device and Method.

\* cited by examiner

INTRALUMINAL DEVICE DELIVERY TECHNIQUE

CROSS REFERENCE TO RELATED APPLICATIONS

This application claims the priority benefits of International Patent Application No. PCT/US2013/029055, filed on Mar. 5, 2013, which claims priority from U.S. patent application Ser. No. 61/607,338, filed on Mar. 6, 2012, and U.S. patent application Ser. No. 61/635,477, filed on Apr. 19, 2012, the disclosures of which are hereby incorporated herein by reference in their entirety.

BACKGROUND OF THE INVENTION

The present invention is directed to a method and apparatus for deploying a medical device and, in particular, to an intraluminal device. While the invention is illustrated with deployment of a bariatric device, it has application for other types of intraluminal devices.

Intraluminal devices are often deployed with a radiopaque marker that is impenetrable to x-rays or other forms of radiation used to ensure that the device is properly positioned. Such device is deployed to the lumen, such as over a guide wire that is first positioned in the lumen. Positioning of the device is effected by the use of fluoroscopy or other form of radiography that detects the radiopaque marker or other portion of the intraluminal device.

SUMMARY OF THE INVENTION

The present application provides a technique for deployment of intraluminal devices, such as bariatric devices, in a manner that is capable of rapid and secure positioning of the device and may be performed without the use of x-rays or other forms of radiation.

A method of deploying an intraluminal device in a mammalian lumen, with the intraluminal device having a device lumen wall that is configured to the size and shape of a portion of the mammalian lumen, according to an aspect of the invention, includes positioning a visualization device through an orifice into the mammalian lumen to a deployment site. A deployment device having the intraluminal device mounted thereto is guided to the deployment site in the mammalian lumen. The intraluminal device is at least partially deployed from the deployment device at the deployment site in the mammalian lumen. The at least partially deployed intraluminal device is positioned at the deployment site with said deployment device while visualizing a position of the intraluminal device with the visualization device.

The deployment device may be guided through the orifice into the mammalian lumen to the deployment site with the visualization device. The deployment device may include a guidance wall surrounding an opening wherein the deployment device is guided by positioning the opening over the visualization device. The intraluminal device may be compressed around the guidance wall. The intraluminal device may be at least partially deployed by unfurling a portion of the intraluminal device from the guidance wall.

The deployment device may further include a deployment sheath surrounding the guidance wall, with the intraluminal device compressed between the deployment sheath and the guidance wall. The intraluminal device may be at least partially deployed by retracting a portion of the deployment sheath overlying the portion of the intraluminal device to be deployed. Deploying of the intraluminal device may be completed by further retracting the deployment sheath overlying a remaining portion of the intraluminal device.

The deployment device may include an actuator attached to the deployment sheath and the deploying may include retracting the actuator with respect to a handle. A stop may be defined between the actuator and the handle, wherein the stop is engaged after the intraluminal device is partially deployed. The visualization device may be a steerable endoscope. The endoscope may be retroflexed at the deployment site. The method may be performed substantially without radiography.

A method of deploying a bariatric device in a mammal, according to another aspect of the invention, includes positioning a visualization device transorally in the stomach. A deployment device having the bariatric device mounted thereto is guided to the stomach. The bariatric device has an esophageal member with an esophageal wall defining an esophageal surface that is configured to generally conform to the shape and size of a portion of the esophagus. The bariatric device has a cardiac member having a cardiac wall defining a cardiac surface that is configured to generally conform to the shape and size of a portion of the cardiac region of the stomach. The bariatric device includes a connector connected with the esophageal member and the cardiac member. The cardiac member is deployed from said deployment device in the stomach and positioned with the deployment device while visualizing a position of the bariatric device with the visualization device.

The deployment device may be guided transorally into the stomach with the visualization device. The deployment device may include a guidance wall surrounding an opening with the deployment device guided by positioning the opening over the visualization device. The bariatric device may be compressed to the guidance wall and wherein the cardiac member deployed by unfurling the cardiac member from the guidance wall. The esophageal member may then be deployed in the esophagus. The esophageal member may be deployed by unfurling the esophageal member from the guidance wall.

The deployment device may include a deployment sheath surrounding the guidance wall, with the bariatric device compressed between the deployment sheath and the guidance wall. The esophageal member and the cardiac member may be positioned on opposite sides of a spacer on the guidance wall. The cardiac member may be deployed by retracting a portion of the deployment sheath overlying the cardiac member. The esophageal member may be deployed by further retracting of the portion of the deployment sheath overlying the esophageal member. The cardiac member may be positioned by rotating the guidance wall and deployment sheath.

The deployment device may include an actuator attached to the deployment sheath and wherein the cardiac member and the esophageal member may be deployed by retracting the actuator with respect to a handle. A stop may be defined between the actuator and the handle, wherein said stop is engaged by the actuator after deploying the cardiac member. The visualization device may be a steerable endoscope. The endoscope may be retroflexed in the stomach. The method may be performed substantially without radiography.

An intraluminal assembly for use with a visualization device, according to yet another aspect of the invention, includes a deployment device having a guidance wall defining a device supporting surface and an opening. The opening is configured to receive the visualization device through the opening. An intraluminal device mounted to the deployment device has a lumen wall that is configured to the size and shape of a portion of a mammalian lumen. The lumen wall is mounted to the guidance wall and the intraluminal device is adapted to be unfurled from said deployment wall in the mammalian lumen. The deployment device is adapted to be guided into the mammalian lumen with the visualization device.

The guidance wall may generally surround the opening. The intraluminal device may be positioned around the guidance wall. The intraluminal device may be compressed on the guidance wall. A deployment sheath may be over the intraluminal device compressed on the guidance wall.

An actuator may be provided that is connected with the deployment sheath. The actuator is adapted to retract the deployment sheath from the intraluminal device in order to deploy the intraluminal device. The opening may be configured to receive a steerable endoscope.

A bariatric assembly for use with a visualization device, according to yet another aspect of the invention, includes a deployment device having a guidance wall defining a device supporting surface and an opening. The opening is configured to receive the visualization device through the opening. A bariatric device is mounted to said deployment device. The bariatric device has an esophageal member with an esophageal wall defining an esophageal surface that is configured to generally conform to the shape and size of a portion of the esophagus, a cardiac member with a cardiac wall defining a cardiac surface that is configured to generally conform to the shape and size of a portion of the cardiac region of the stomach and a connector connected with the esophageal member and the cardiac member. The esophageal wall and the cardiac wall are mounted to the guidance wall. The cardiac member is adapted to be unfurled from the deployment wall in the stomach and the esophageal member is adapted to be unfurled from the deployment wall in the esophagus. The deployment device is adapted to be guided into the esophagus and stomach with the visualization device in the opening.

The deployment wall may generally surround the opening. The bariatric device may be positioned around the guidance wall and may be compressed on the guidance wall. A deployment sheath may be provided over the bariatric device compressed on the guidance wall. An actuator may be provided that is connected with the deployment sheath and adapted to retract the deployment sheath with respect to the bariatric device in order to deploy the bariatric device. The actuator may be adapted to be retracted with respect to a handle in order to deploy the bariatric device. A stop may be provided that inhibits further retraction of the actuator with respect to the handle after the cardiac member is deployed. The stop may be adapted to be selectively overcome and the actuator further retracted with respect to the handle in order to deploy the esophageal member. A spacer may be provided on the guidance wall separating the cardiac member from the esophageal member. The opening may be configured to receive a steerable endoscope.

A bariatric assembly, according to yet another aspect of the invention, includes a deployment device having a guidance wall defining a device supporting surface and a bariatric device mounted to the deployment device. The bariatric device has an esophageal member with an esophageal wall defining an esophageal surface that is configured to generally conform to the shape and size of a portion of the esophagus, a cardiac member with a cardiac wall defining a cardiac surface that is configured to generally conform to the shape and size of a portion of the cardiac region of the stomach and a connector connected with the esophageal member and the cardiac member. The esophageal wall and the cardiac wall are compressed to the guidance wall. The deployment device is adapted to selectively allow the cardiac member to be unfurled from the guidance wall in the stomach and is adapted to selectively allow the esophageal member to be unfurled from the guidance wall in the esophagus.

The deployment device may be adapted to be guided to the stomach with an endoscope and at least the cardiac member visualized by retroflexing the endoscope in the stomach.

Because embodiments of the invention allow an intraluminal device, such as a bariatric device, to be deployed in the lumen, such as the gastro-intestinal tract, with a visualization device guiding placement of the device in the lumen, the need for radiography may be avoided. This allows the method to be carried out without the bulky and expensive equipment associated with radiography, such as fluoroscopy. In this manner, the method may be carried out in a more common out-placement procedure room. This not only reduces risk to the patient and practitioners, but eliminates the need for shielding of the patient and practitioners. This allows the procedure to be carried out faster.

These and other objects, advantages and features of this invention will become apparent upon review of the following specification in conjunction with the drawings.

DESCRIPTION OF THE PREFERRED EMBODIMENT

Figure 1:
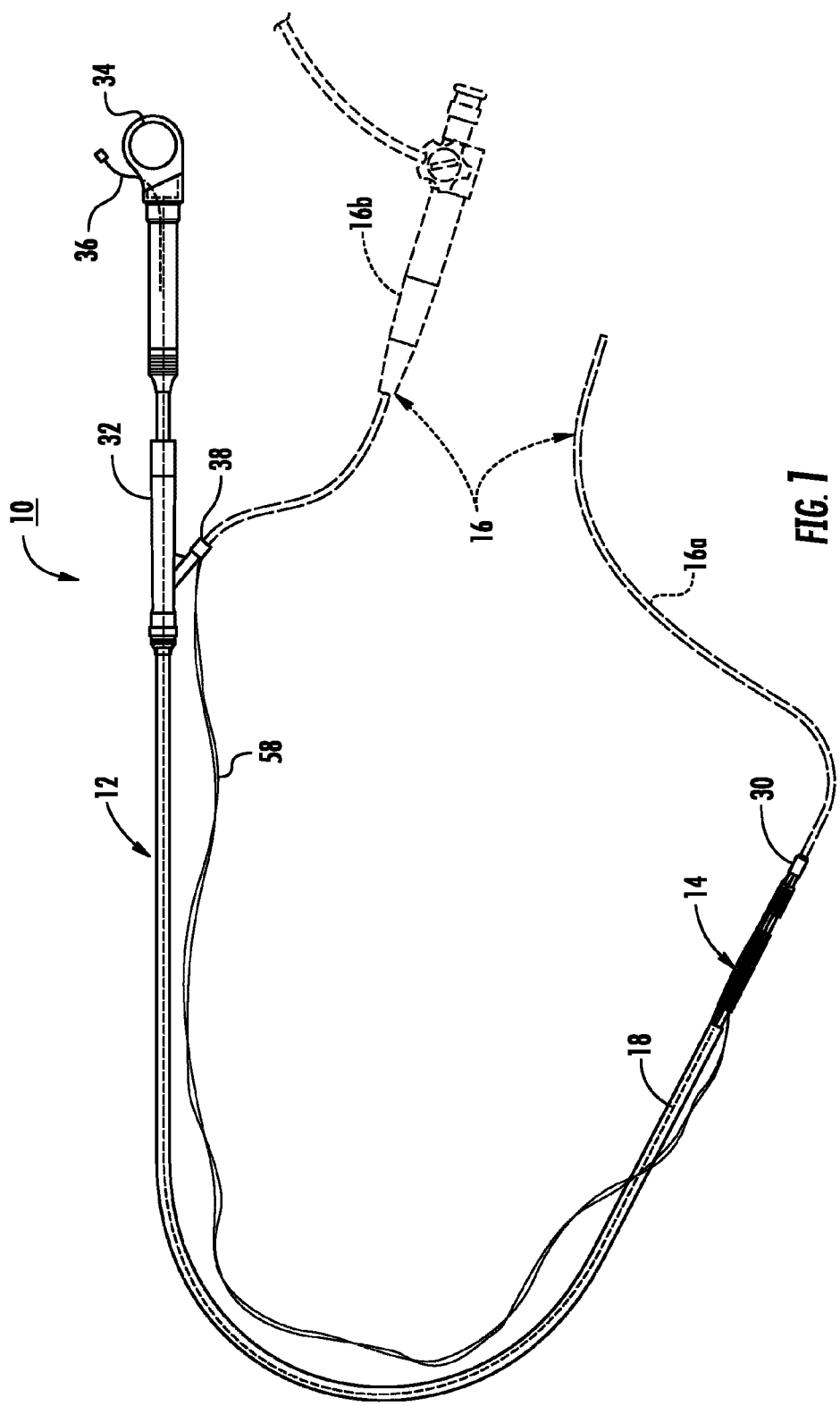
FIG. 1 is a perspective view of an intraluminal assembly, such as a bariatric assembly, according to an embodiment of the invention.

Referring now to the drawings and the illustrative embodiments depicted therein, an intraluminal assembly, such as a bariatric assembly 10, includes a deployment device 12 and an intraluminal device, such as a bariatric device 14 (FIG. 1). Intraluminal assembly 10 is configured to be guided to a deployment site and visualized during deployment by a visualization instrument, such as an endoscope 16. Such endoscope has a manipulating portion 16b and a slender elongated portion 16a that extends to the procedure site and is capable of being steered and manipulated from manipulating portion 16b. Such endoscope is conventional and is commercially available from various sources. In the illustrated embodiment, a miniature endoscope is used that is capable of being retro-flexed using known techniques. Bariatric device 14 is of the type disclosed in commonly assigned U.S. Pat. Nos. 7,846,174 and 8,100,931; U.S. Patent Application Publication No. 2010/0030017 A1 entitled BARIATRIC DEVICE AND METHOD; International Patent Application Publication No. WO 2012/044917 A1 entitled INTRALUMINAL DEVICE AND METHOD; and International Patent Application Publication No. WO 2012/162114 entitled INTRALUMINAL DEVICE AND METHOD WITH ENHANCED ANTI-MIGRATION, the disclosures of which are hereby incorporated herein by reference in their entireties.

Deployment device 12 includes a flexible shaft 18 that has a length that is greater than the length of the esophagus with a through-opening 22 extending the length of the shaft. Opening 22 has a diameter that is large enough to accommodate the elongated portion 16a of endoscope 16. Shaft 18 includes a deployment portion 30 that receives intraluminal device 14 in a compressed form, as will be described in more detail below. Shaft 18 further includes a proximal portion 24 that has a larger diameter than deployment portion 20 in order to provide ripcord openings 26 and plenum-space 28 for passage of wrapping filament 29, both of which are used to removeably retain intraluminal device 14 in a compressed state as will be described below. Proximal portion 24 has a filler 25, such as a polymer, to provide flexible structure to shaft 18.

Intraluminal device 14, which is illustrated as a bariatric device, has a cardiac member 40, an esophageal member 46 and a connector 50 connecting the cardiac and esophageal members (FIGS. 8-11 and 14). Cardiac member 40 is made up of a cardiac wall 42 that is configured to the size and shape of the cardiac portion of the stomach and has a cardiac surface 44 that contacts and stimulates receptors in the cardiac region of the stomach. A resilient mesh 43 in wall 42 provides structure to the wall while allowing it to be compressed for deployment and to be self-unfurling for use. Intraluminal device 14 further includes an esophageal member 46 having an esophageal wall 48 that is configured to the size and shape of the distal portion of the esophagus and has an esophageal surface 50 that contacts the esophageal wall. A resilient mesh 49 allows esophageal member 46 to be compressed for deployment and to be self-unfurling for use.

Figure 8:
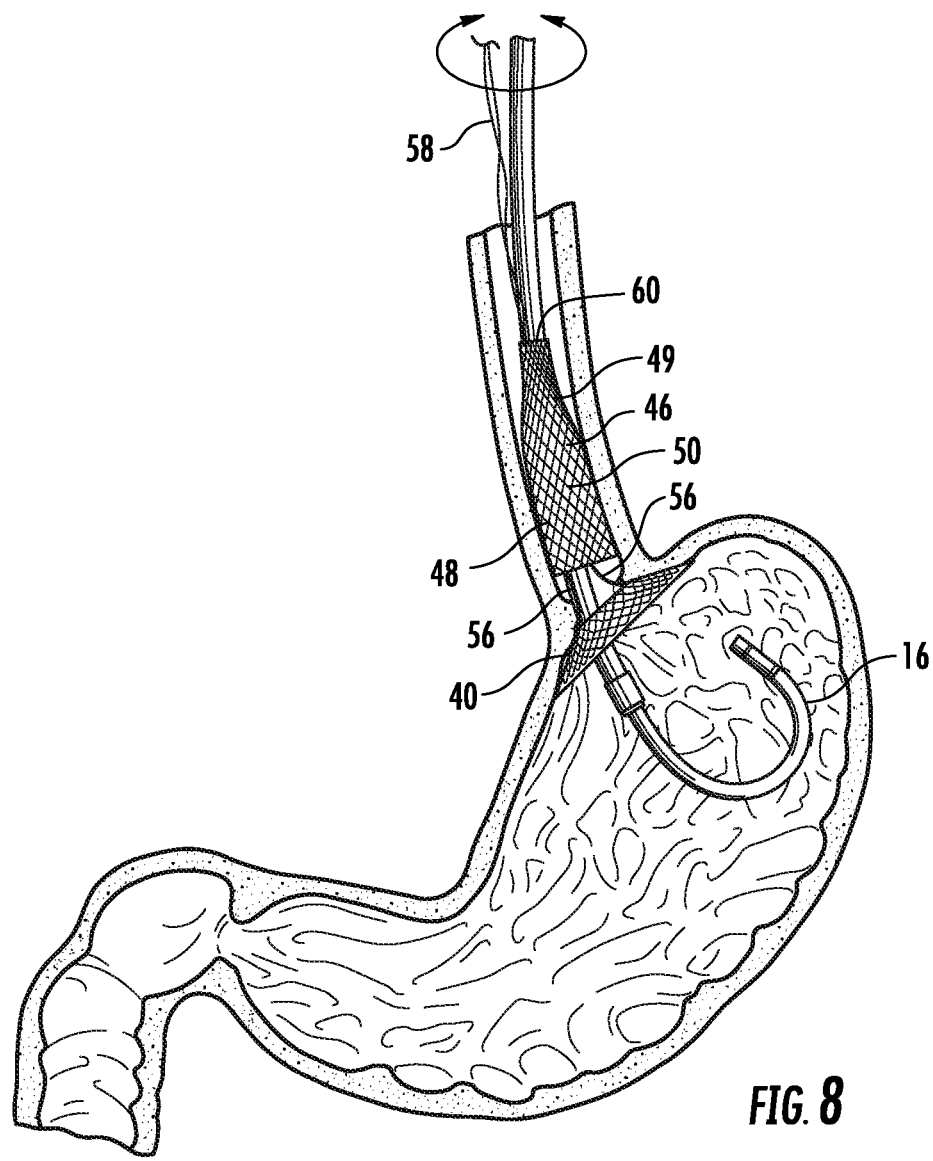
FIG. 8 is the same view as FIG. 2 illustrating unfurling and positioning of the esophageal member.

A connector 54 connects esophageal member 46 and cardiac member 40 in a manner that does not substantially interfere with the operation of the GE junction. In the illustrated embodiment, connector 54 is made up of two struts, or tension members, 56 that pass through the GE junction and transmit force from esophageal member 46 to keep cardiac surface 44 in contact with the cardiac portion of the stomach. Struts 56 may be oriented in various orientations, such as side-to-side in a frontal plane or anterior-posterior in a sagittal plane. If oriented in a frontal plane, one strut oriented at the greater curve may be longer in order to allow for the angled orientation of the cardiac member with respect to the esophageal member. Also, the strut 56 that is at the greater curve area of the stomach may be of a more flexible material than the other strut in order to conform to the curvature of the greater curve. The struts are illustrated as being of equal length. The cardiac member will easily orient itself with respect to the esophageal member about a pivot axis that passes through both of the struts. Thus, the physician can orient the intraluminal device while partially deployed, i.e., with the cardiac member unfurled, but the esophageal member still compressed on shaft 18. With the physician visualizing the physiology, namely, arrangement of the esophagus to the stomach in the particular patient, shaft 18 can be rotated as shown in FIG. 8 to orient the bariatric device to allow the cardiac member to pivot with respect to the esophageal member without twisting struts 56 about each other.

Figure 2:
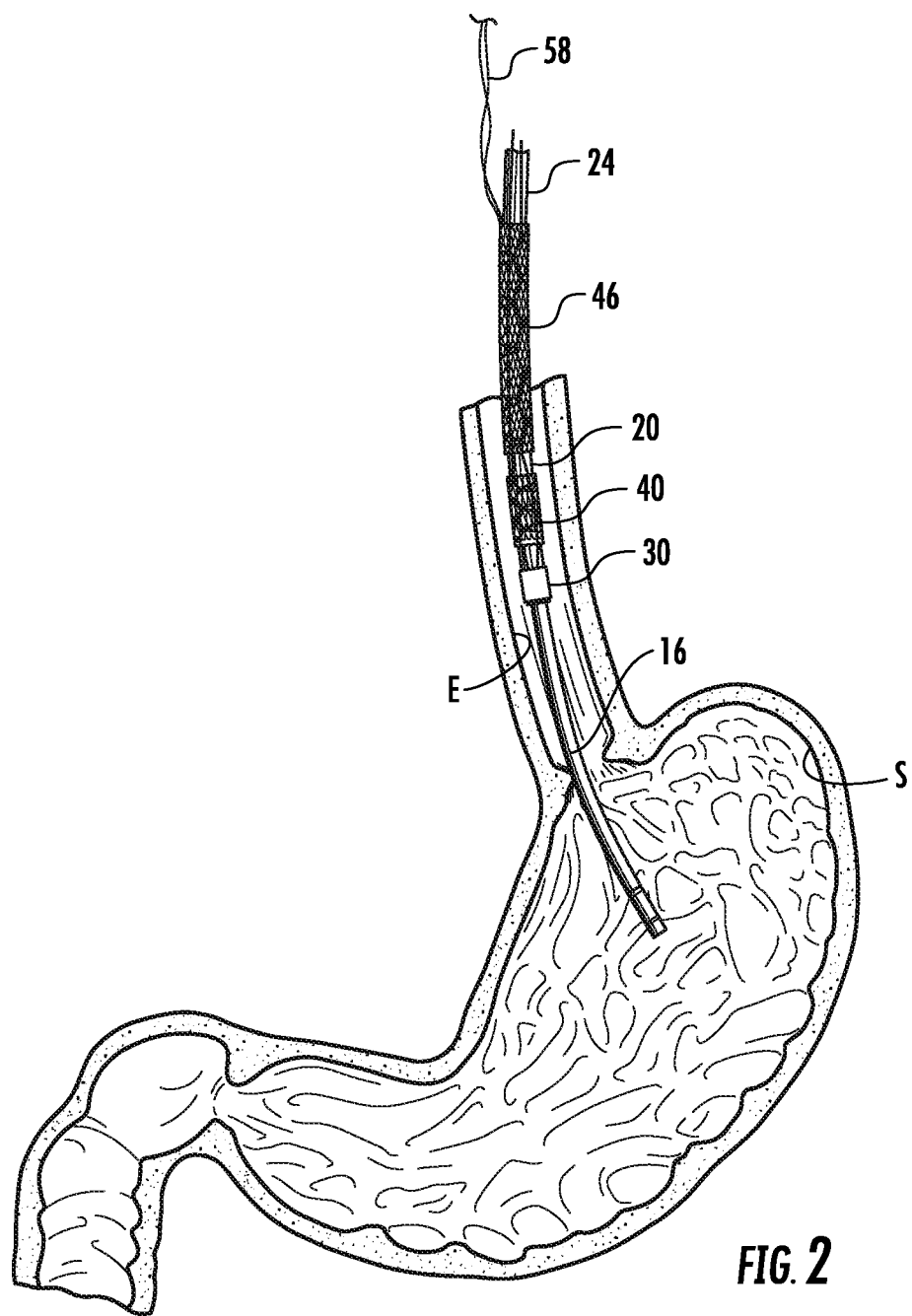
FIG. 2 is a frontal view illustrating guidance of the intraluminal assembly toward the deployment site using an endoscope.
Figure 3:
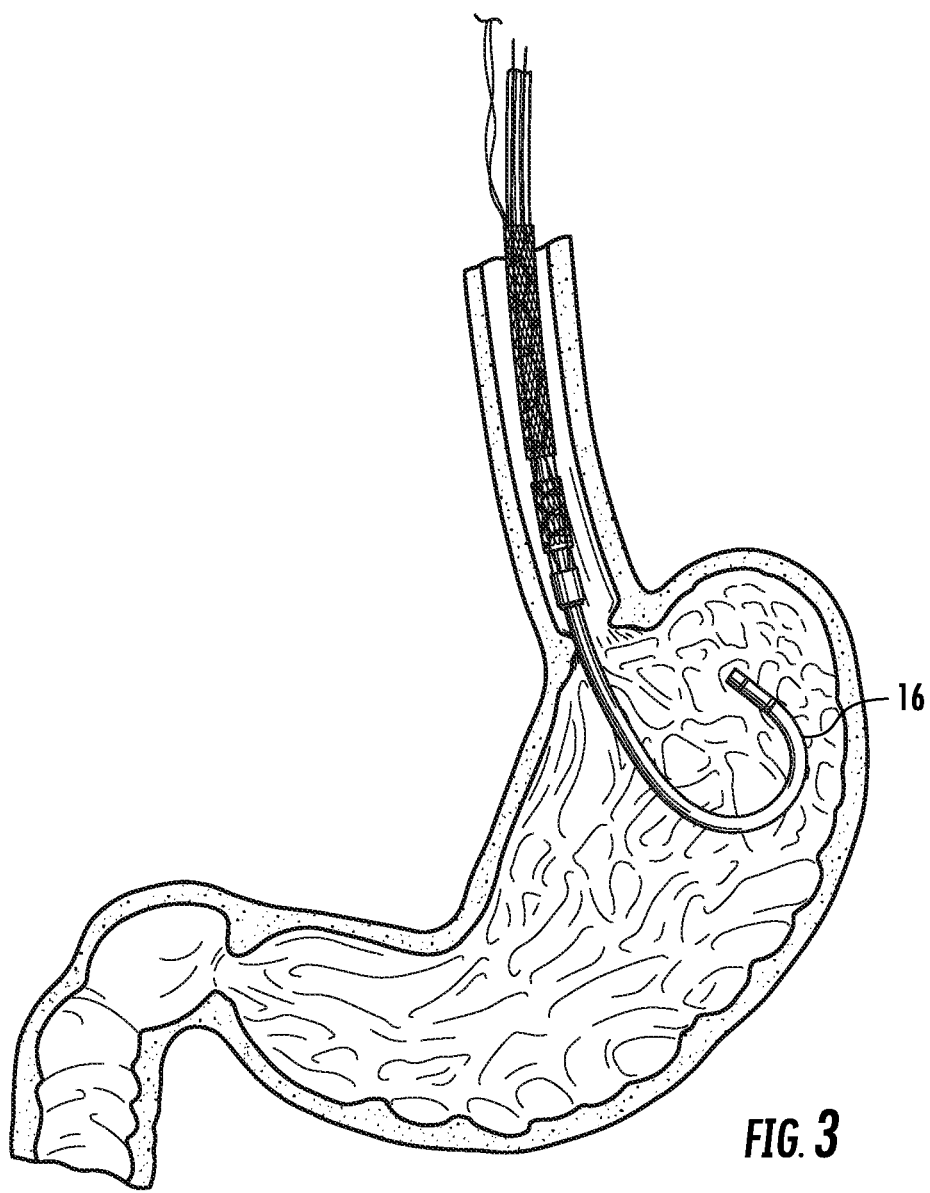
FIG. 3 is the same view as FIG. 2 illustrating retro-flexing of the endoscope.
Figure 4:
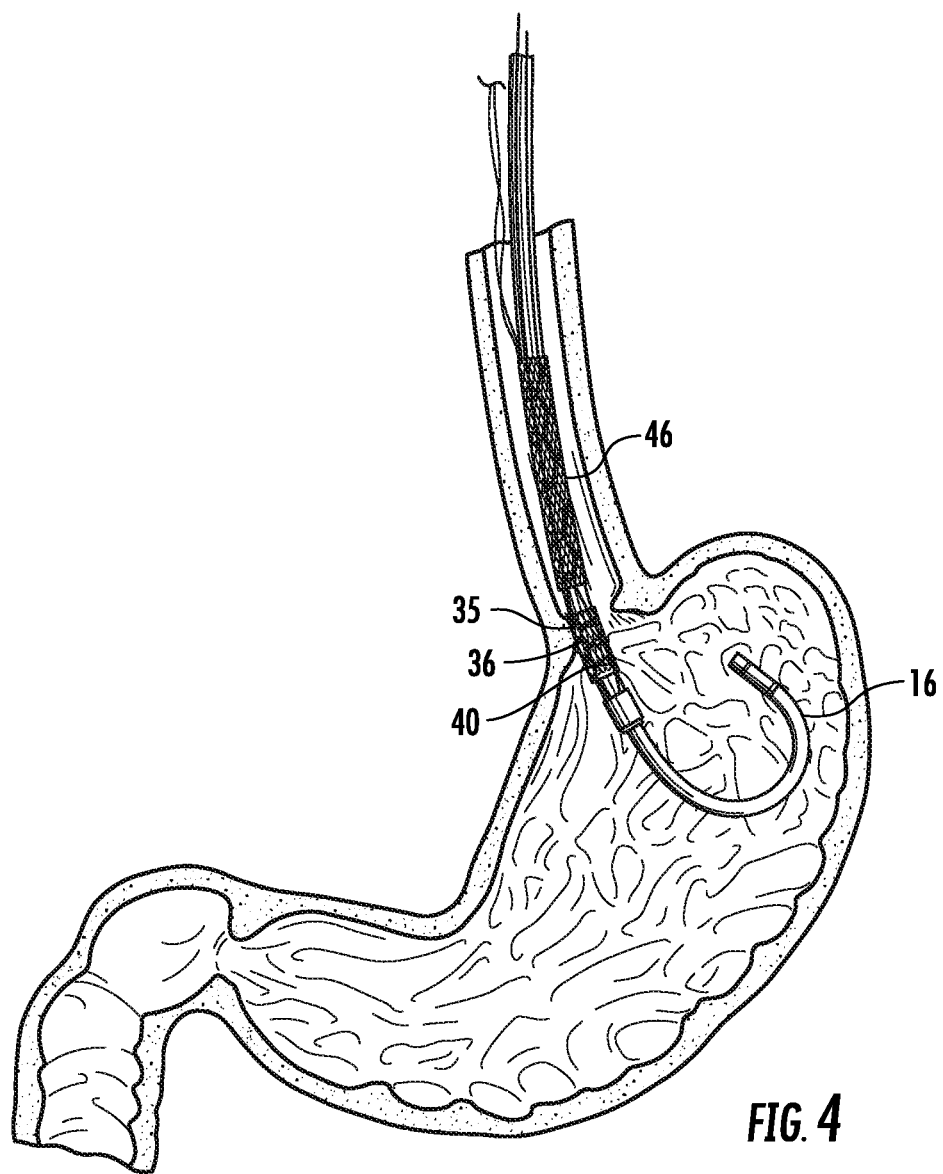
FIG. 4 is the same view as FIG. 2 illustrating locating of the cardiac member in the stomach.
Figure 6:
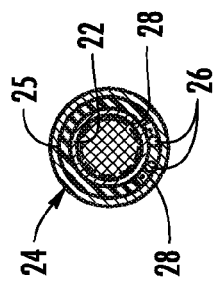
FIG. 6 is a sectional view taken along the lines VI-VI in FIG. 5.
Figure 7:
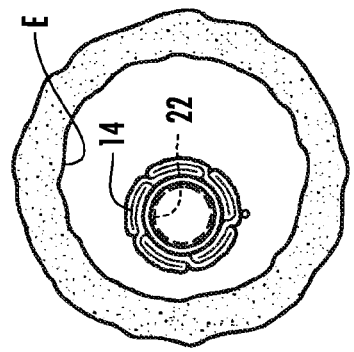
FIG. 7 is a sectional view taken along the lines VII-VII in FIG. 5.

The method of deploying intraluminal device, such as bariatric device 14, in a lumen, such as the gastro-intestinal tract, is as follows. A visualizing device, such as endoscope 16, is inserted in opening 22 in deployment device 12, such as through a port 38 that connects with opening 22, as illustrated in FIG. 1. With a portion of endoscope 16 extending distally beyond the distal end of shaft 18, deployment device with elongated portion 16a of the endoscope extending distally from the end of the device is inserted into the esophagus E with or without an overtube in place, as illustrated in FIG. 2. In the illustrated embodiment, no overtube is used. Once endoscope 16 is guided through the esophageal-gastric (EG) junction under direct visualization of the EG junction through the endoscope, endoscope 16 terminates in the stomach S. The endoscope is retroflexed to view the EG region, as illustrated in FIG. 3. Endoscope 16 provides a guide to guide bariatric assembly 10 past the EG junction into the GE region by the physician, or other medical person, manipulating a handle 32 at a proximal end of deployment device 12 while cardiac member 40 is visualized through retroflexed endoscope 16. With cardiac member 40 positioned in the stomach, as seen in FIGS. 3 and 4, a ripcord actuator 34 associated with the cardiac member is pulled. This retracts a deployment sheath in the form of a ripcord 35 from wrapping filament 36 wound around the cardiac member, thus freeing the wrapping filament to fall away and the cardiac member to unfurl under its own outward bias. Ripcord 35 may be retracted into proximal portion 24 of flexible shaft 18 or fully retracted from shaft 18. A proximal portion of wrapping filament 36 at handle 32 may be used to fully retract the wrapping filament through plenum 28.

Figure 5:
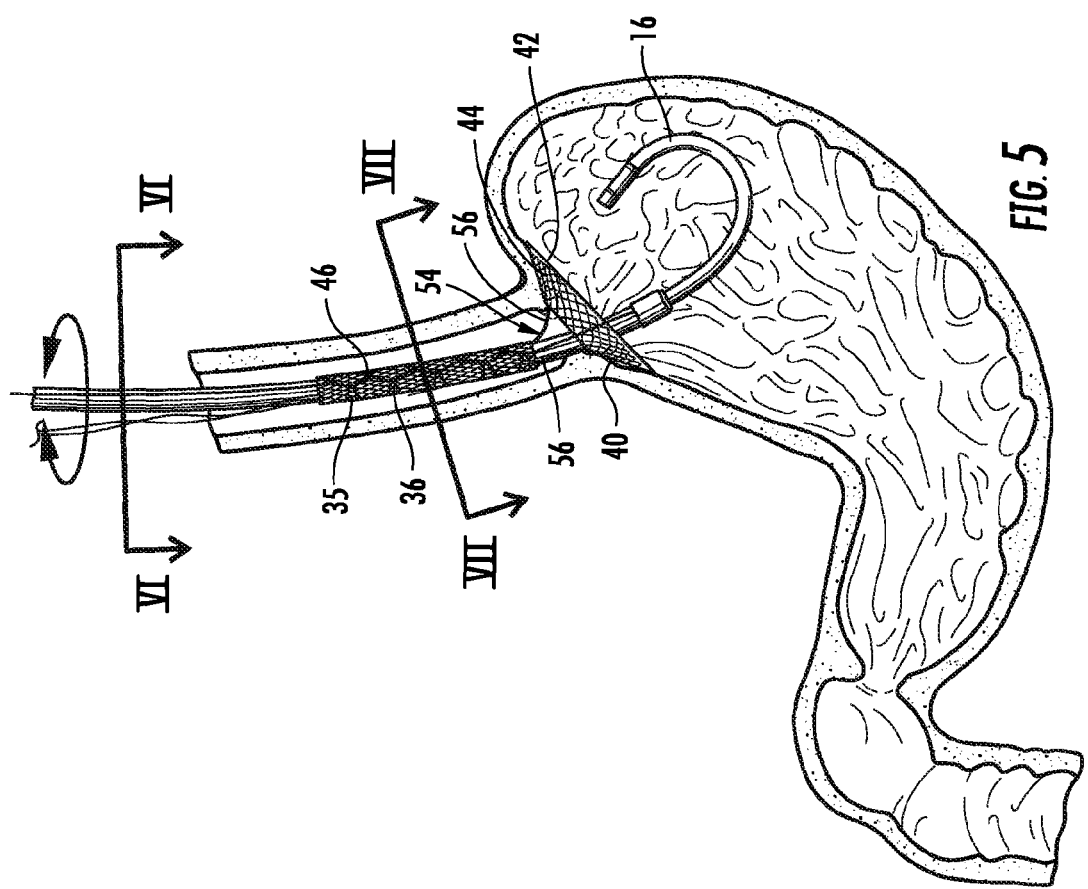
FIG. 5 is the same view as FIG. 2 illustrating unfurling and positioning of the cardiac member at the cardiac region of the stomach.

With cardiac member 40 unfurled, handle 32 may be manipulated by rotating shaft 18 and proximally translating the shaft in order to position cardiac member 40 in a desired orientation and tensioned against the cardiac region of stomach S, as illustrated in FIG. 5. Visual markings may be provided on cardiac member 40 to facilitate this alignment. However, fluoroscopy is not used.

Figure 9:
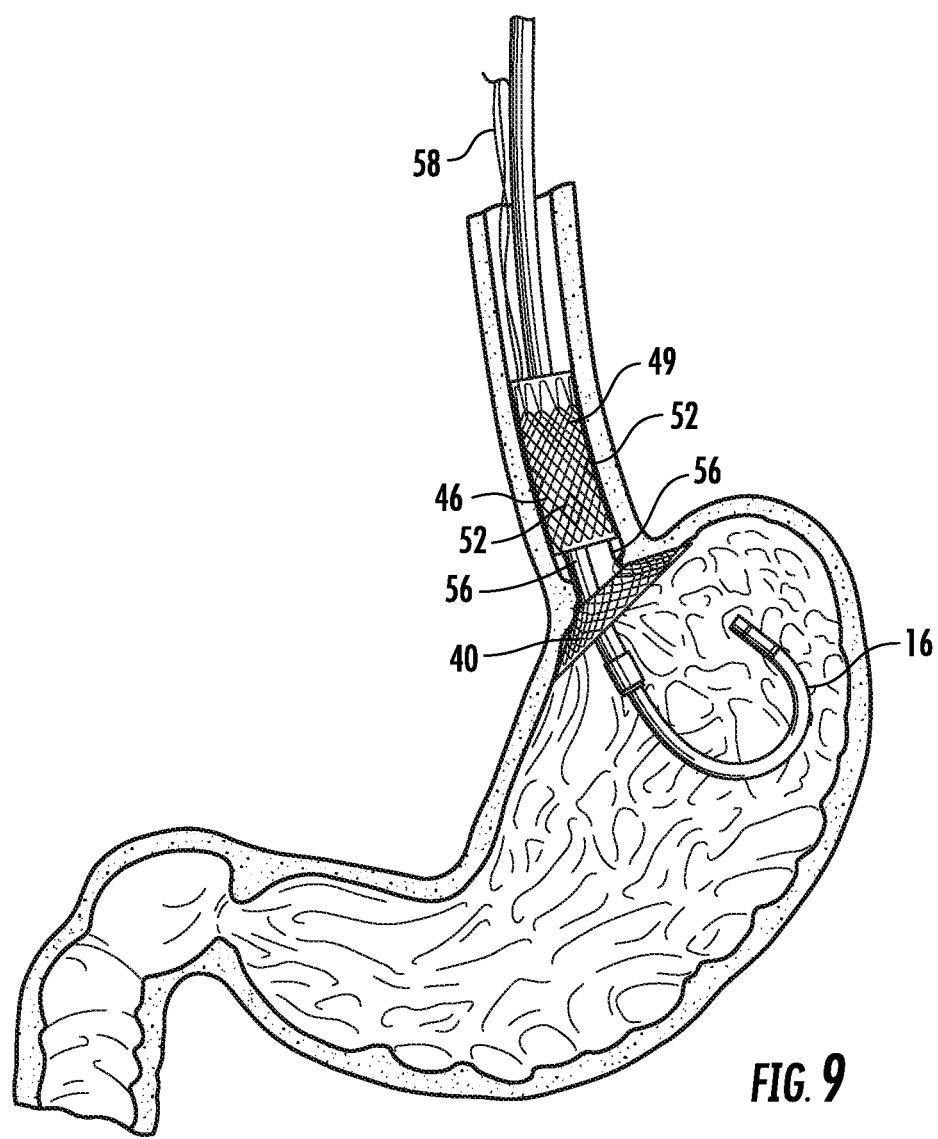
FIG. 9 is the same view as FIG. 2 illustrating detachment of the esophageal member from the deployment device.
Figure 11:
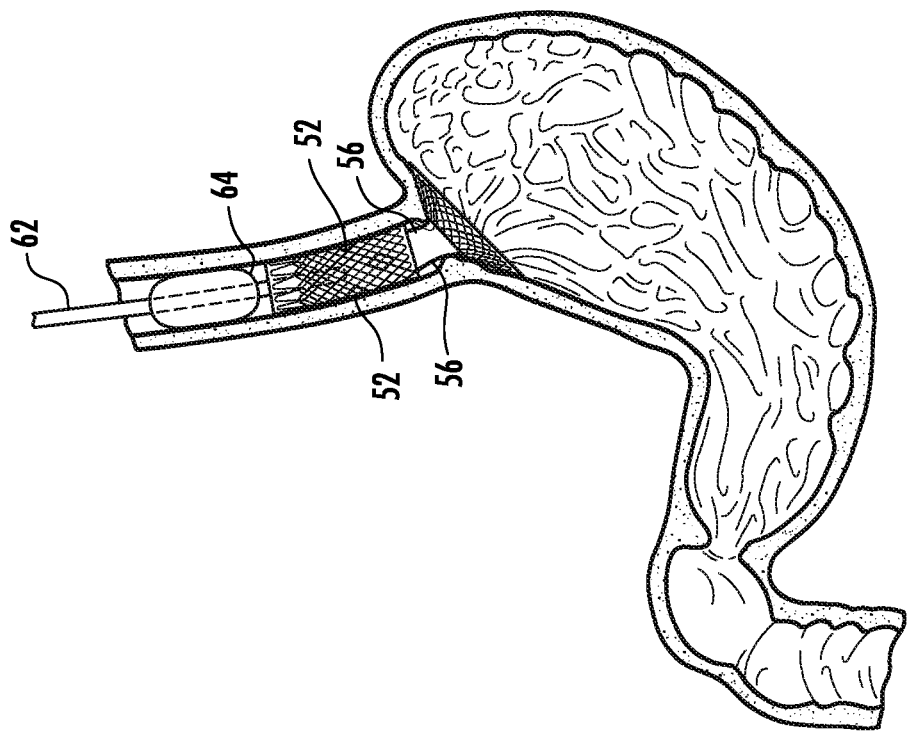
FIG. 11 is the same view as FIG. 2 illustrating seating of the esophageal member.
Figure 10:
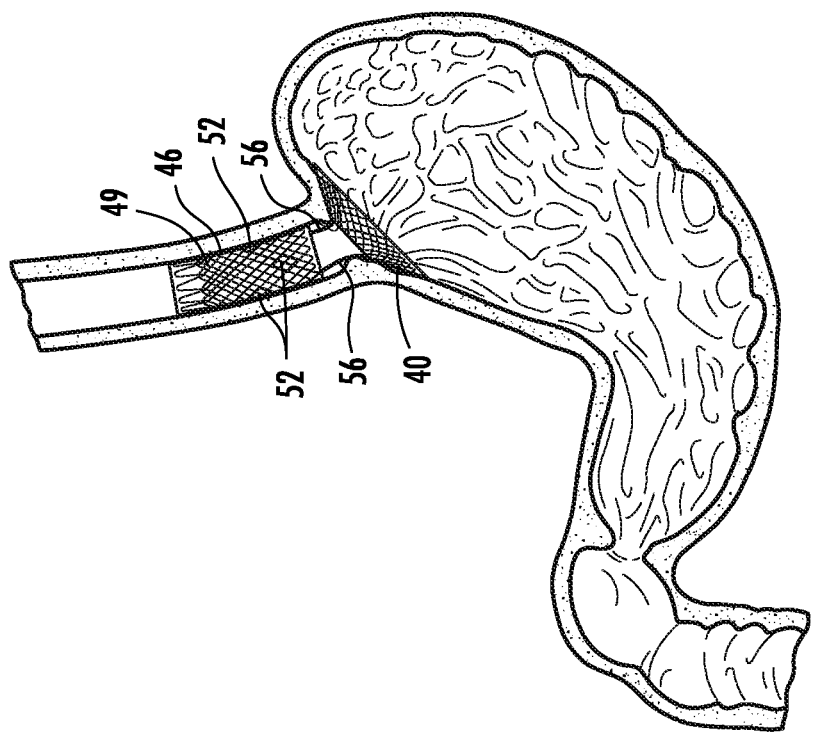
FIG. 10 is the same view as FIG. 2 illustrating the bariatric device in position with the deployment device and endoscope removed.
Figure 12:
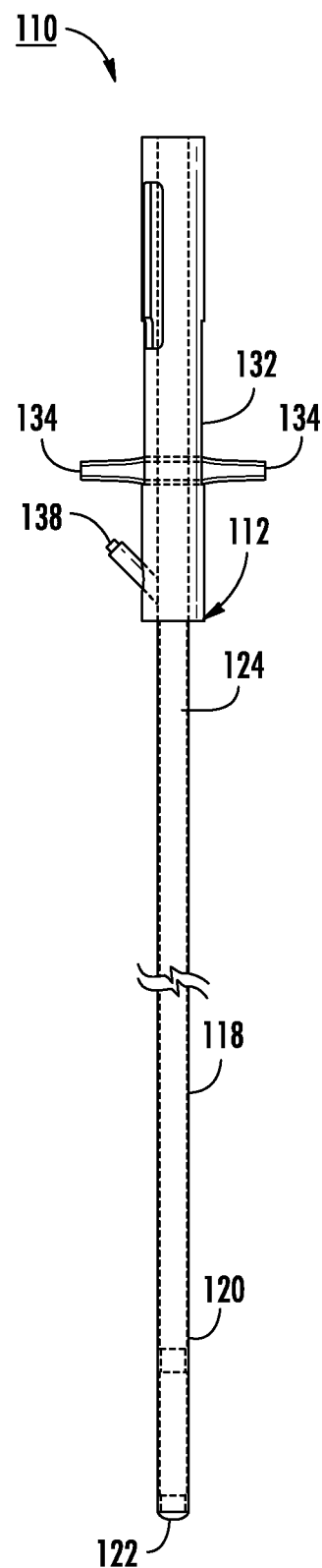
FIG. 12 is a perspective view of an intraluminal assembly, such as a bariatric assembly, according to an alternative embodiment of the invention.

With cardiac member 40 in position against the cardiac region of the stomach, the physician further retracts the deployment sheath by pulling the other ripcord actuator 34 (not seen, but positioned behind the ripcord actuator 34 in FIG. 1), the ripcord 35 holding the wrapping filament 36 surrounding esophageal member 46 is pulled away allowing esophageal member 46 to unfurl under its own outward bias. Both the ripcord and wrapping filament are withdrawn in the manner previously described. However, esophageal member 46 remains attached proximally with an attachment filament 58 that is looped through holes (not shown) in deployment portion 20 and the esophageal member 46 in a weave or stitched pattern. This allows esophageal member 46 to be rotated, if necessary, or pulled in order to position the esophageal member and adjust the pressure on cardiac member 40 by way of connector 54, as illustrated in FIG. 8. Attachment filament 58, which is routed external of shaft 18, is then detached by pulling on one end of the filament, as seen in FIG. 9. While attachment filament 58 is shown only for use in manipulating esophageal member 46, another attachment filament may be used between cardiac member 40 and deployment portion 20 to assist manipulation of the cardiac member after it is unfurled.

With bariatric device 14 positioned in the GE region of the recipient, the esophageal member 46 is seated to the esophagus. Esophageal member 46 has one or more mucosal capture openings 52. Openings 52, in the illustrated embodiment, are made up of a series of contiguous cells of the mesh that are not covered by the outer silicone cover over mesh 49. This allows the mucosal lining of the esophagus, along with its blood supply, to be pooched into the diamond-shaped openings in the mesh, under the outward pressure of esophageal wall 48 against the esophagus using the principles disclosed in commonly assigned International Patent Application Publication No. WO 2008/100984 A2, entitled Mucosal Capture Fixation of Medical Device, the disclosure of which is hereby incorporated herein by reference. Such captured mucosa will bridge and overgrow the mesh wires separating these open cells. In the illustrated embodiment, four (4) contiguous open cells are provided for each opening 52 formed as a diamond-shaped pattern of diamond-shaped cells. However, it should be understood that other patterns may be used. Openings 52 may be distributed about esophageal wall 48 in a manner that they are separated from each other according to the wavelength of peristaltic waves travelling along the esophagus using the principles disclosed in commonly owned pending International Patent Application Publication No. WO 2012/162114, entitled INTRALUMINAL DEVICE AND METHOD WITH ENHANCED ANTI-MIGRATION, the disclosure of which is hereby incorporated herein by reference in its entirety. This further resists distal migration of esophageal member 46 from the peristalsis of the esophagus.

Esophageal member 46 may be seated by applying a vacuum or suction source to a portion of the esophagus. This is accomplished by placing a vacuum or suction source 62 in the esophagus at approximately the proximal end of the esophageal member. A seal, such as an inflatable balloon 64, may be provided to avoid air from being drawn through the esophagus. Vacuum source 62 may be routed via an open channel in endoscope 16 and may be applied as the endoscope is being withdrawn. Alternatively, a larger double-lumen endoscope may be used as a vacuum or suction source, in which case a separate seal 64 may not be needed. Alternatively, a separate vacuum tube may be used.

With a suction applied to the interior of esophageal member 46, the GE junction (or EG junction) is drawn proximally into closer engagement with the distal end portion of esophageal member 46, thus reducing the tendency for distal migration. Also, the suction tends further pull the mucosa into openings 52 along with the blood supply for the mucosa. This provides additional mechanical binding because more of the mucosa is drawn through the openings. Also, this tends to cause the mucosa to become irritated and swollen which speeds up the inflammatory process thereby encouraging the mucosa to grow over the exposed wire of mesh 49 according to the principles disclosed in commonly owned U.S. Patent Application Publication No. 2010/0198237 A1 entitled MUCOSAL CAPTURE FIXATION OF MEDICAL DEVICE, the disclosure of which is hereby incorporated herein by reference.

Thus, the seating process may serve either or both to draw the GE junction tighter to the distal end portion of esophageal member 46 and to enhance mucosal capture in openings 52. The process of applying suction can be repeated until the desired result is achieved. The suction can also, or alternatively, be applied directly to the mucosa pooched into each opening 52. Alternatively or additionally, other techniques may be used to promote inflammatory response in the pooched mucosa, such as roughening it with a wire brush or treating it with an agent, such as a sclerosant, all as described in the '237 patent application publication.

In an alternative embodiment, an intraluminal assembly, such as a bariatric assembly 110, includes a deployment device 112 having a flexible shaft 118 that has a length that is greater than the length of the esophagus with a through-opening 122 extending the length of the shaft (FIGS. 12-18). In particular, flexible shaft 118 has a length extending from the teeth to the esophageal-gastric (EG) junction of a "typical", or average, mammal, such as a human. Opening 122 has a diameter that is large enough to accommodate the elongated portion 16a of endoscope 16. For example, in the illustrative embodiment, opening 122 has a diameter of about 6.5 millimeters to fit over an endoscope shaft having an outer diameter 18 of about 5.9 millimeters. Deployment device 112 includes a deployment portion 120 that receives intraluminal device 14 in a compressed form, as will be described in more detail below. Shaft 118 further includes a proximal portion 124 that is connected with an operator handle 132 with an actuator 134 both of which are used to removeably retain intraluminal device 14 in a compressed state, as will be described below.

Shaft 118 includes a guidance wall 170 which is formed as a cylinder and defines through-opening 122 down the center of the cylinder. Guidance wall 170 terminates distally in a round tip 131 in order to present a smooth surface when passing through the GE junction. Bariatric device 14 is compressed onto guidance wall 170 by a deployment sheath 172. A spacer 180 separates esophageal member 46 from cardiac member 40 when they are compressed against guidance wall 170. Deployment sheath 172 surrounds guidance wall 170 and is sufficiently larger in diameter than guidance wall 170 such that intraluminal device 14 can be compressed between the deployment sheath 172 and guidance wall 170. Deployment device 112 further includes a handle 132 that is connected with guidance wall 170, such as at proximal portion 124 of shaft 118, and an actuator 134 that is moveable with respect to handle 132 and is connected with deployment sheath 172. Deployment sheath 172 can be axially displaced with respect to guidance wall 170 so that movement of actuator 134 with respect to handle 132 causes deployment sheath 172 to be axially moved with respect to guidance wall 170. In this manner, retraction of actuator 134 causes deployment sheath 172 to be retracted with respect to guidance wall 170. Bariatric device 14 can be deployed in stages by retracting the actuator to retract a portion of said deployment sheath 172 overlying a portion of the bariatric device to device 14 be deployed. Deployment of the bariatric device 14 can be completed by further retracting deployment sheath 172 from overlying the remaining portion of bariatric device 14.

Figure 13:
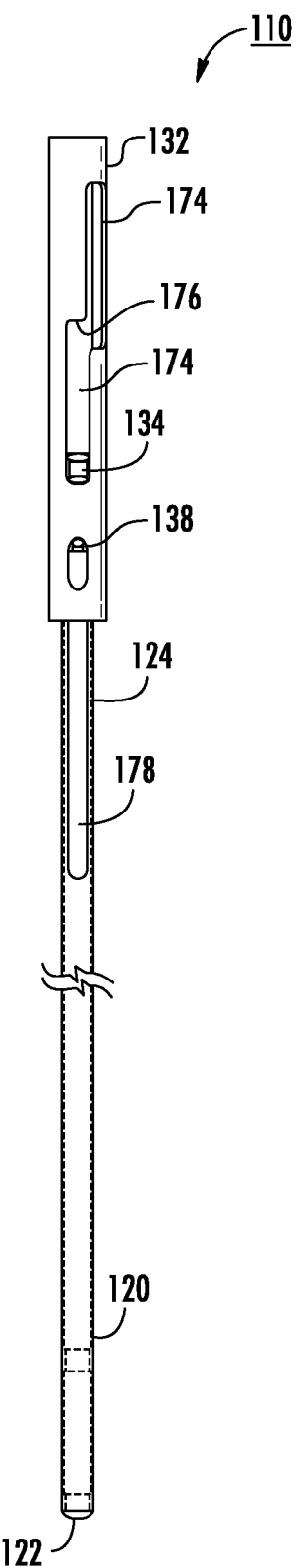
FIG. 13 is a perspective view of the intraluminal assembly in FIG. 12 at an orientation that is about 45 degrees offset from the view in FIG. 12.
Figure 16:
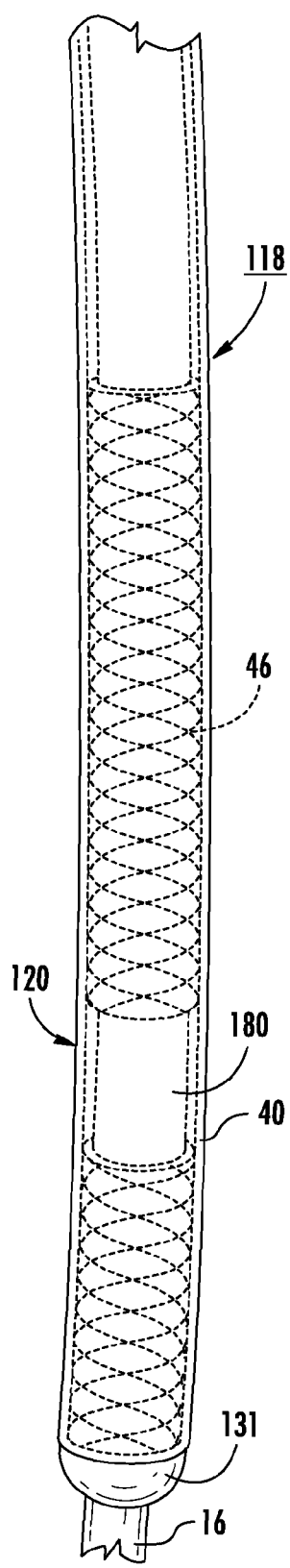
FIG. 16 is an enlarged perspective view of a distal portion of the intraluminal assembly in FIGS. 12 and 13.
Figure 18:
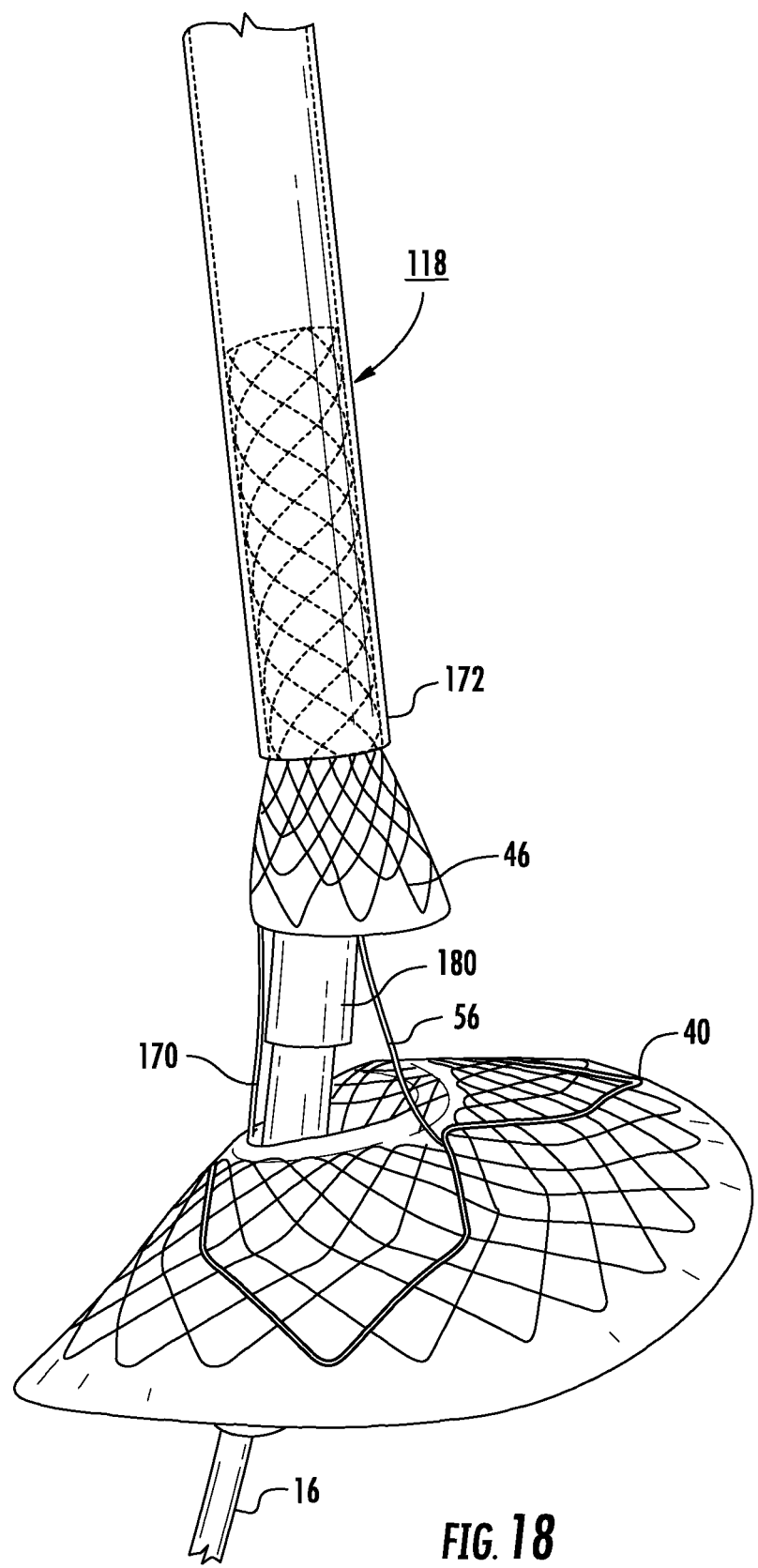
FIG. 18 is the same view as FIG. 16 with the cardiac member deployed and the esophageal member partially deployed.

As can be best seen in FIG. 13, actuator 134 is moveable within a channel 174 of handle 132. Channel 174 has a abrupt offset at 176 which defines a stop defined between actuator 134 and handle 132. Thus, with actuator 134 fully extended distally, as illustrated in FIG. 13, deployment sheath 172 fully extends over guidance wall 170 which compresses the entire bariatric device 14 between the deployment sheath and guidance wall, as best seen in FIG. 16. Upon retracting actuator 134 using the physician's fingers while grasping handle 132, sheath 132 is retracted sufficiently to expose cardiac member 40, as best seen in FIG. 18. Because actuator 134 will strike offset 76 and stop further movement, the esophageal member 46 will remain compressed between deployment sheath 172 and guidance wall 170, as best seen in FIG. 18.

Figure 17:
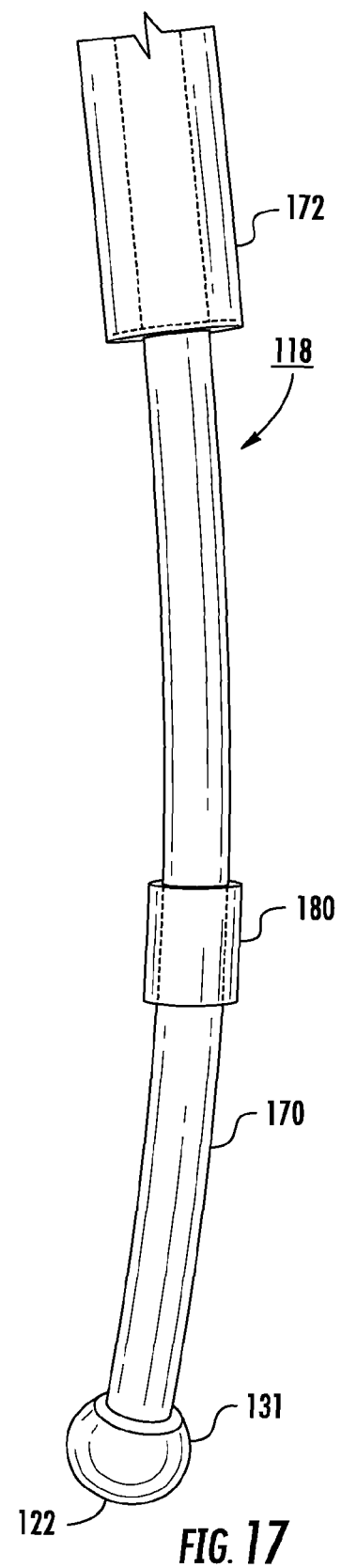
FIG. 17 is the same view as FIG. 16 with the deployment sheath retracted and bariatric device removed to reveal internal details of the deployment device thereof.

After the physician is satisfied that cardiac member 40 is properly positioned against the cardiac portion of the stomach, as viewed by endoscope 16 being retroflexed to view the cardiac member, actuator 134 is moved laterally to bypass offset, or stop, 176 which allows the actuator to continue to be proximally retracted after the bariatric device 14 has been partially deployed. This further retraction of actuator 134 with respect to handle 132 causes deployment sheath 172 to be further proximally retracted with respect to guidance wall 170, as seen in FIG. 17, thus allowing esophageal member 46 to unfurl thus completing the deployment process. One or more attachments, such as loops of suture material (not shown), can extend proximally from the top of esophageal member 46 through the space between deployment sheath 172 and guidance wall 70 and out the proximal end of deployment device 12. These attachments extend external the recipient and allow the physician to pull up on the esophageal member to snug the cardiac member against the cardiac region of the stomach or to temporarily restrain bariatric device 14 such as when reinserting the endoscope 16 to carry out suctioning of mucosa pooching through mucosal capture openings, or the like. Once it is determined that the attachments are no longer needed, the loop of suture material can be cut and the suture material withdrawn by tugging on one end thereof.

Figure 15:
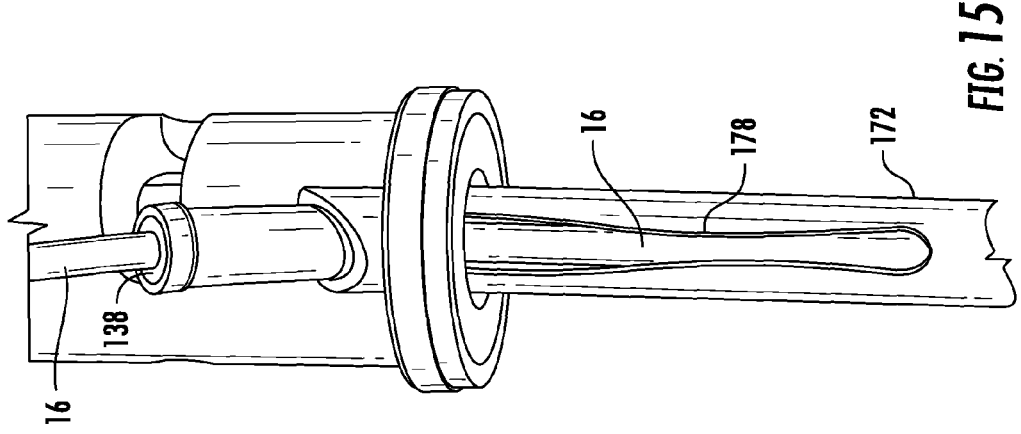
FIG. 15 is an enlarged perspective view of a proximal portion of the intraluminal assembly in FIGS. 12 and 13.
Figure 14:
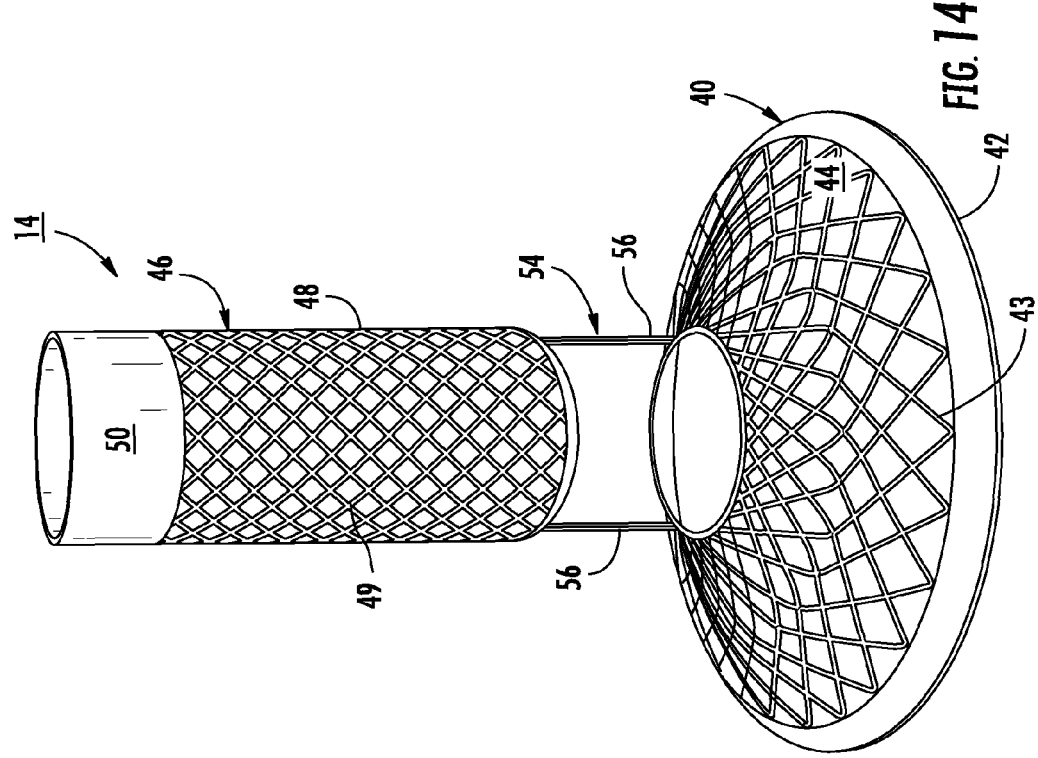
FIG. 14 is a perspective view of a bariatric device that can be deployed according to the various embodiments of the invention.

The method of deploying intraluminal device, such as bariatric device 14, in a lumen, such as the gastro-intestinal tract, using deployment device 112 is as follows. A visualizing device, such as endoscope 16, is inserted in opening 122 in deployment device 112, such as through a port 138 that connects with opening 122, as illustrated in FIG. 15. In order to allow deployment sheath 172 to be withdrawn proximally, a slit 178 is defined in deployment sheath 172 through which endoscope 16 can pass. Elongated portion 16a of the endoscope is inserted until a distal end thereof extends passed opening 122 at a distal end of shaft 118 and first the endoscope and then the deployment device passed into the esophagus E with or without an overtube in place. Once endoscope 16 approaches the EG junction, it can be used to visualize the distal EG junction to guide the endoscope as the endoscope passes through the EG junction, but before the distal end of shaft 118 passes through the EG junction. The endoscope 16 is used to guide shaft 118 of the deployment device through the EG junction. It may be desirable to extend a sufficient amount of endoscope 16 into the stomach and retroflex the endoscope in order to visualize shaft 118 passing through the EG junction with a sufficient length of shaft 118 in the stomach to deploy cardiac member 40. Alternatively, the endoscope can be used to guide shaft 118 through the EG junction and retroflex the endoscope only after both are in the stomach.

Thus, it can be seen that endoscope 16 provides a guide to guide bariatric assembly 110 into the GE region by the physician, or other medical person, manipulating a handle 132 at a proximal end of deployment device 112 while cardiac member 40 is visualized through retroflexed endoscope 16. With cardiac member 40 positioned in the stomach, actuator 134 is retracted until it reaches stop or offset 176. This retracts deployment sheath 172 from around the compressed cardiac member 40, thus freeing the cardiac member to unfurl under its own outward bias, as best seen in FIG. 18. Once it is visualized, thorough retroflexed endoscope 16, that cardiac member 40 is adequately seated against the cardiac portion of the stomach by manipulating handle 132, actuator 134 may then be retracted further along channel 174 beyond offset 176. This causes deployment sheath 172 to retract further thus exposing the entire bariatric device including esophageal member 46.

Since the seating of cardiac member 40 in the proper position in the stomach will also properly position esophageal member 46 in the esophagus, the further retraction of deployment sheath 172 will cause esophageal member 46 to unfurl under the internal outward bias of the esophageal wall. With the esophageal wall outward bias against the mucosa of the esophagus, mucosa pooching into mucosal capture openings will provide anchoring of the esophageal member in the esophagus which will cause cardiac member 40 to apply a stress to the cardiac portion of the stomach through connector 54. Esophageal member 46 may be seated further by applying a vacuum or suction source to a portion of the esophagus as previously described. This is accomplished by placing a vacuum or suction source 62 in the esophagus at approximately the proximal end of the esophageal member. Likewise, a filler material, such as collagen or hyaluronic acid, may be injected into bulging mucosa to further increase the size of the bulging mucosa and provide additional mucosal capture to anchor esophageal member 46 in the esophagus.

The techniques disclosed herein can be used for deploying other types of intraluminal devices in a mammalian lumen. For example, a medical device fixation tool of the type disclosed in U.S. Pat. No. 8,372,087 B2, the disclosure of which is hereby incorporated herein by reference, can be guided using a visualization device, such as an endoscope, in order to avoid the need for fluoroscopy to fix a medical device according to the principles disclosed in the '087 patent. Optionally, a balloon can be positioned around the shaft of the fixation tool in order to seal the esophagus when insufflating the stomach such as using an insufflating channel of the endoscope. Other applications will be apparent to the skilled artisan when apprised of the teachings herein.

While the foregoing description describes several embodiments of the present invention, it will be understood by those skilled in the art that variations and modifications to these embodiments may be made without departing from the spirit and scope of the invention, as defined in the claims below. The present invention encompasses all combinations of various embodiments or aspects of the invention described herein. It is understood that any and all embodiments of the present invention may be taken in conjunction with any other embodiment to describe additional embodiments of the present invention. Furthermore, any elements of an embodiment may be combined with any and all other elements of any of the embodiments to describe additional embodiments.

The embodiments of the invention in which an exclusive property or privilege is claimed are defined as follows:

1. A method of deploying a bariatric device in a mammal, said bariatric device having an esophageal member with an esophageal wall defining an esophageal surface that is configured to generally conform to the shape and size of a portion of the esophagus, a cardiac member with a cardiac wall defining a cardiac surface that is configured to generally conform to the shape and size of a portion of the cardiac region of the stomach and a connector connected with said esophageal member and said cardiac member, said method comprising:

positioning a visualization device transorally in the stomach;

guiding a deployment device having the bariatric device mounted thereto and a deployment sheath overlying the bariatric device to the stomach;

deploying the cardiac member from said deployment device in the stomach by retracting a portion of said deployment sheath overlying the cardiac member; and positioning the cardiac member with said deployment device while visualizing orientation of the cardiac member within the stomach with said visualization device including re-orienting the cardiac member in the stomach by rotating said deployment device if the cardiac member is not properly oriented; and deploying the esophageal member in the esophagus by further retracting of said portion of said deployment sheath overlying the esophageal member after the cardiac member is properly oriented.

2. The method as claimed in claim 1 including guiding said deployment device transorally into the stomach with said visualization device.

3. The method as claimed in claim 2 wherein said deployment device comprises a guidance wall surrounding an opening wherein said guiding said deployment device comprises positioning said opening over said visualization device.

4. The method as claimed in claim 3 wherein said bariatric device is compressed to said guidance wall and wherein said deploying the cardiac member includes unfurling the cardiac member from said guidance wall.

5. The method as claimed in claim 4 wherein said bariatric device is compressed between said deployment sheath and said guidance wall.

6. The method as claimed in claim 5 wherein said deploying said esophageal member includes unfurling the esophageal member from said guidance wall.

7. The method as claimed in claim 5 wherein said esophageal member and said cardiac member are positioned on opposite sides of a spacer on said guidance wall.

8. The method as claimed in claim 1 wherein said visualization device comprises a steerable endoscope.

9. The method as claimed in claim 8 including retroflexing said endoscope in the stomach.

10. A method of deploying a bariatric device in a mammal, said bariatric device having an esophageal member with an esophageal wall defining an esophageal surface that is configured to generally conform to the shape and size of a portion of the esophagus, a cardiac member with a cardiac wall defining a cardiac surface that is configured to generally conform to the shape and size of a portion of the cardiac region of the stomach and a connector connected with said esophageal member and said cardiac member, said method comprising:

positioning a visualization device transorally in the stomach;

guiding a deployment device having the bariatric device mounted thereto to the stomach;

deploying the cardiac member from said deployment device in the stomach; and positioning the cardiac member with said deployment device while visualizing a position of said bariatric device with said visualization device;

wherein said deployment device includes an actuator attached to said deployment sheath and a stop defined between said actuator and said handle, and wherein said deploying the cardiac member and said deploying the esophageal member includes retracting said actuator with respect to a handle wherein said stop is engaged by said actuator after deploying said cardiac member including overcoming said stop in order to deploy said esophageal member including a channel for said actuator wherein said stop is defined by an offset in said channel and said stop is overcome by moving said actuator laterally past said offset.

11. A bariatric assembly for use with a visualization device, said bariatric assembly comprising:

a deployment device having a guidance wall defining a device supporting surface and an opening, said opening configured to receive the visualization device through said opening; and a bariatric device mounted to said deployment device, wherein said bariatric device having an esophageal member with an esophageal wall defining an esophageal surface that is configured to generally conform to the shape and size of a portion of the esophagus, a cardiac member with a cardiac wall defining a cardiac surface that is configured to generally conform to the shape and size of a portion of the cardiac region of the stomach and a connector connected with said esophageal member and said cardiac member;

wherein said esophageal wall and said cardiac wall are positioned against said device supporting surface by a deployment sheath, wherein said cardiac member is unfurled from said deployment wall in the stomach and said esophageal member is unfurled from said deployment wall in the esophagus by retraction of said deployment sheath with respect to said guidance wall, wherein said deployment device is adapted to be guided into the esophagus and stomach with the visualization device in said opening; and said deployment device having a handle and an actuator connected with said deployment sheath wherein said actuator is retracted with respect to said handle to retract said deployment sheath with respect to said guidance wall in order to deploy said bariatric device and a stop that inhibits further retraction of said actuator with respect to said handle after said cardiac member is deployed wherein said stop is selectively overcome and said actuator further retracted with respect to said handle in order to deploy said esophageal member including a channel for said actuator wherein said stop is defined by an offset in said channel and said stop is overcome by moving said actuator laterally past said offset.

12. The bariatric assembly as claimed in claim 11 wherein said guidance wall generally surrounds said opening.

13. The bariatric assembly as claimed in claim 12 wherein said bariatric device is positioned around said guidance wall.

14. The bariatric assembly as claimed in claim 11 wherein said deployment sheath compresses said bariatric device on said supporting surface.

15. The bariatric assembly as claimed in claim 11 including a spacer on said guidance wall, said spacer separating said cardiac member from said esophageal member.

16. The bariatric assembly as claimed in claim 11 wherein said opening is configured to receive a steerable endoscope.

* * * * *